(12) United States Patent
Nakao

(10) Patent No.: US 6,913,610 B2
(45) Date of Patent: Jul. 5, 2005

(54) ENDOSCOPIC RETRACTOR INSTRUMENT AND ASSOCIATED METHOD

(75) Inventor: Naomi Nakao, New York, NY (US)

(73) Assignee: Granit Medical Innovations, Inc., New York, NY (US)

( * ) Notice: Subject to any disclaimer, the term of this patent is extended or adjusted under 35 U.S.C. 154(b) by 330 days.

(21) Appl. No.: 09/978,413

(22) Filed: Oct. 16, 2001

(65) Prior Publication Data

US 2003/0074015 A1 Apr. 17, 2003

(51) Int. Cl.[7] ............................................. A61M 29/00
(52) U.S. Cl. ............................. 606/192; 604/101.01
(58) Field of Search ................................. 606/192, 110, 606/114, 115, 193, 194, 112, 197, 111; 604/101.01, 101.03, 101.04, 101.05, 96.01, 509; 623/8; 600/207

(56) References Cited

U.S. PATENT DOCUMENTS

| | | | | |
|---|---|---|---|---|
| 4,241,735 A | * | 12/1980 | Chernov | 606/192 |
| 5,354,270 A | * | 10/1994 | Wilk et al. | 604/500 |
| 5,411,479 A | * | 5/1995 | Bodden | 604/101.03 |
| 5,630,843 A | * | 5/1997 | Rosenberg | 623/8 |
| 5,634,883 A | * | 6/1997 | Chin et al. | 600/204 |
| 6,048,330 A | * | 4/2000 | Atala | 604/96.01 |
| 6,409,723 B1 | * | 6/2002 | Edwards | 606/41 |
| 6,425,877 B1 | * | 7/2002 | Edwards | 604/21 |

\* cited by examiner

Primary Examiner—Julian W. Woo
Assistant Examiner—Victor Nguyen
(74) Attorney, Agent, or Firm—R. Neil Sudol; Henry D. Coleman; William J. Sapone

(57) ABSTRACT

An endoscopic retractor instrument has (a) a plurality of parts movably connected to one another, (b) componentry for mounting the parts in a collapsed or reduced-size configuration to a flexible and steerable insertion member of an endoscope, and (c) one or more actuation elements operatively connected to the parts for enabling a movement of the parts relative to one another so that the parts assume an enlarged or expanded configuration for spreading internal tissues of a patient. The movable parts of the retractor instrument may be inflatable balloon parts enabling insertion of the retractor in a substantially collapsed configuration and a later expansion at the site of interest.

17 Claims, 2 Drawing Sheets

ENDOSCOPIC RETRACTOR INSTRUMENT AND ASSOCIATED METHOD

BACKGROUND OF THE INVENTION

This invention related to a medical device and to an associated medical technique. More particularly, this invention relates to an endoscopic instrument and to an endoscopic method.

Flexible endoscopes are inserted into the digestive tract for diagnostic and therapeutic purposes. Endoscopes generally include a light guide for transmitting optical-wavelength electromagnetic radiation into the patient. Images are captured, typically via lenses and an optical fiber bundle or a charge-coupled device, whereby a user can visually inspect the inner walls or surfaces of the digestive tract. One common objective of endoscopic investigations in the digestive tract is to detect the presence of polyps. Where a polyp is visually detected, particularly in the colon, it should be severed, captured, and removed from the patient. Alternatively, particularly where the polyp may be a malignant cancer, the polyp may be severed and captured for extraction from the patient.

One problem frequently encountered by endoscopists is that folds of tissues in the digestive tract and particularly the colon can obscure polyps so that they can be overlooked. The colon is often collapsed and may be partially draped over a lesion. In order to distend the walls of the colon, the endoscopist often pumps air into the organ. However, if too much air is introduced, the colon could perforate. Also, the patient is made quite uncomfortable with introduction of substantial amounts of air.

Another problem with visualization during an endoscopic procedure is that polyps sometimes bleed when they are severed. If the lesion site cannot be adequately visualized, it is difficult to contain and control the bleeding.

OBJECTS OF THE INVENTION

It is an object of the present invention to provide an endoscopic instrument assembly which is particularly suitable for use with flexible endoscopes during investigations of the digestive or gastrointestinal tract.

A further object of the present invention is to provide such an instrument assembly which is inexpensive and/or easy to use.

It is another object of the present invention to provide an endoscopic procedure for facilitating visual inspection of the digestive tract.

These and other objects of the invention will be apparent from the drawings and descriptions herein.

SUMMARY OF THE INVENTION

An endoscopic retractor instrument assembly comprises, in accordance with a particular embodiment of the present invention, an insertion or deployment tube insertable into a biopsy channel of an endoscope, a balloon or bladder having a pair of expandable or inflatable end members and at least one expandable or inflatable spacer member connecting the end members to one another, the balloon or bladder being disposed in a collapsed configuration inside the tube. An inflation element is operatively coupled with the balloon or bladder for inflating the balloon or bladder from the collapsed configuration to an expanded use configuration in which the spacer member pushes the end members apart from one another.

Naturally, the end members expand radially or transversely. This transverse expansion of the instrument enables the application of pressure to the colon wall or other portion of a digestive tract to expand the organ and smooth out folds. This facilitates inspection and the performance of endoscopic operations on target tissues inside the patient.

The inflation element of the retractor instrument assembly may include an additional tube or conduit connected to the balloon or bladder for enabling the feeding of a pressurizing fluid such as saline solution or a gas (air) to the balloon or bladder. This inflation tube is typically a flexible line extending back along the biopsy channel of the endoscope to a pressurization device (e.g., a syringe) outside of the patient.

The inflation element may further include a one-way valve disposed between the inflation tube and the balloon or bladder. The valve automatically prevents the escape of the pressurizing fluid from the balloon or bladder and thus facilitates the use of the instrument in an endoscopic procedure. The valve may be disposed inside the balloon or bladder or alternatively in a nipple or nub element connected thereto. In any case, the inflation tube may be removably connected to the balloon or nipple, for instance, via a screw connection or a frangible link. The extraction of the inflation tube upon the disconnection thereof from the balloon clears the site of interest and thereby facilitates the performance of additional diagnostic or therapeutic procedures.

In a preferred form of this particular embodiment of an endoscopic retractor instrument assembly, the inflatable end members are toroidal or ring-shaped. In addition, the spacer member is one of a plurality of elongate expandable or inflatable spacer members each having one end connected to and communicating with one of the end members and an opposite end connected to and communicating with another one of the end members. Moreover, at least one of the elongate spacer members may be provided with a semi-rigid stiffener rod which facilitates ejection of the balloon or bladder from the distal end of the insertion or deployment tube by a pusher rod.

An endoscopic retractor instrument assembly comprises, in accordance with a more general description of the present invention, (a) a plurality of parts movably connected to one another, (b) componentry for mounting the parts in a collapsed or reduced-size configuration to a flexible and steerable insertion member of an endoscope, and (c) one or more actuation elements operatively connected to the parts for enabling a movement of the parts relative to one another so that the parts assume an enlarged or expanded configuration for spreading internal tissues of a patient.

The mounting componentry may includes elements for attaching the parts of the retractor instrument assembly to an outer surface of the insertion member. The parts may be removably attached to the insertion member, for instance, by a balloon clamp.

The relatively movable parts of the endoscopic retractor instrument assembly may include, as discussed above, a plurality of expandable or inflatable balloon or bladder parts.

A medical method in accordance with the present invention utilizes an endoscopic retractor instrument and a flexible endoscope having an insertion member. The method comprises (I) inserting a distal end portion of the insertion member into a patient, (ii) deploying the retractor instrument from the distal end portion of the insertion member upon inserting of the distal end portion into the patient, and (iii) thereafter operating the retractor instrument to engage an inner wall of an internal organ of the patient so as to spread the inner wall.

Where the retractor instrument includes a plurality of parts movably connected to one another and where the retractor instrument is attached to an outer surface of the insertion member during the inserting of the distal end portion into the patient, the operating of the retractor instrument includes moving the parts relative to one another to increase an effective diameter of the retractor instrument. Where the internal organ is tubular such as the colon, so that the inner wall is roughly cylindrical, the expanding of the retractor instrument enables a stretching of the organ to remove folds from the inner wall. This facilitates a rigorous visual inspection of the internal organ, as well as any endoscopic surgical procedures on the tissues of the organ.

Where the retractor instrument includes a plurality of prongs arranged in a cylindrical configuration on a ring member surrounding the insertion member during the inserting of the distal end portion into the patient, the operating of the retractor instrument including spreading the prongs so that the retractor instrument assumes a substantially conical configuration.

Where the retractor instrument includes a balloon or bladder member, the operating of the retractor member includes feeding a fluid to the balloon or bladder to inflate the balloon or bladder from a collapsed configuration to an expanded use configuration. Then the deploying of the retractor instrument includes ejecting the retractor instrument in the collapsed configuration from a tubular member into the patient.

The present invention enables the insertion of a retractor deep inside a patient through a natural body opening. At the site of interest, whether a diagnostic or surgical site, the retractor is expanded to a configuration many times larger than the collapsed insertion configuration, thereby enabling a substantial spreading of internal tissues.

A retractor pursuant to the present invention remains by itself in the colon or other lumen or generally inside the patient and does not require continued support by or connection to the insertion instrument, whether that instrument is a flexible endoscope, a trocar sleeve or other device. This independent support capability of the retractor allows the operating surgeon to use the insertion instrument for the deployment of other surgical tools.

DETAILED DESCRIPTION OF THE PREFERRED EMBODIMENTS

Figure 1:
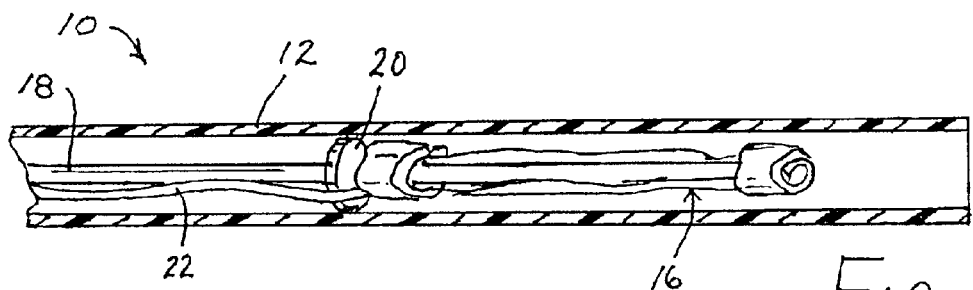
FIG. 1 is a schematic longitudinal cross-sectional view of an endoscopic retractor instrument assembly in accordance with the present invention, showing a balloon or bladder member in a collapsed insertion configuration.
Figure 2:
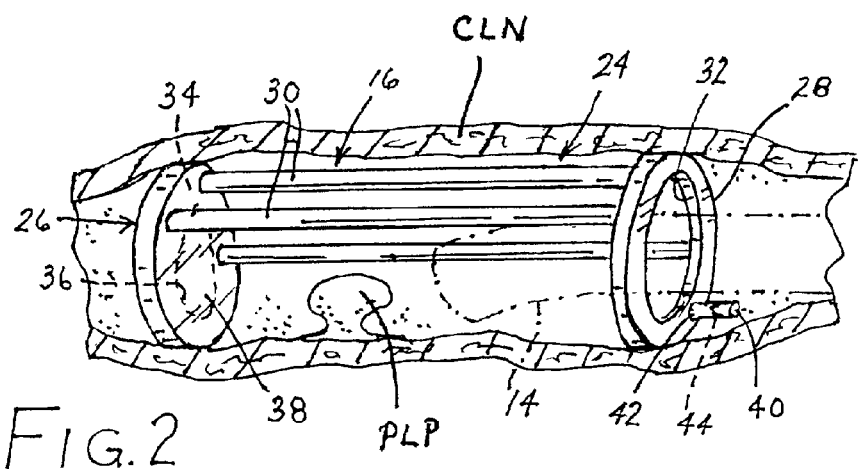
FIG. 2 is a schematic perspective view of the balloon or bladder member of FIG. 1, showing the balloon or bladder in an inflated use configuration inside a colon.

As illustrated in FIG. 1, an endoscopic retractor instrument assembly 10 comprises an insertion or deployment tube 12 insertable into a biopsy channel (not shown) of an endoscope insertion member 14 (see FIG. 2). The assembly 10 additionally comprises a balloon or bladder 16 disposed in a collapsed configuration inside a distal end portion (not separately designated) of the insertion or deployment tube 12. A pusher rod 18 extending through tube 12 is formed at a distal end with a flange 20 engageable with a proximal end of the collapsed balloon 16. To eject the collapsed balloon 16 from the distal end of tube 12, pusher rod 18 is shifted in the distal direction (away from the user).

The retractor assembly 10 further comprise a flexible conduit or tubule 22 extending through tube 12 to balloon 16. Conduit or tubule 22 is connected at a distal end to balloon 16 and communicates therewith to enable channeling of a pressurization fluid, e.g., a saline solution or a gas such as air, to the balloon for purposes of inflating the balloon. At a proximal end, tubular 22 is connected to a source of the pressurization fluid, such as a syringe (not shown) or canister of carbon dioxide (not shown).

During an endoscopic operation, a distal end portion of endoscope insertion member 14 is inserted into a patient, for instance, into the colon CLN (FIG. 2) of the patient. After the distal end of endoscope insertion member 14 attains a selected location or site inside the bowel or colon CLN, as determined, for instance, through a visual inspection of the bowel wall using the optical componentry of the endoscope, insertion or deployment tube 12 is shifted distally through the biopsy channel (not shown) of the endoscope so that a distal end of tube 12 extends into colon CLN. At that juncture, rod 18 is shifted in the distal direction relative to tube 12 to eject balloon 12 into colon CLN. At that point in the procedure, the balloon 16 is still in its collapsed or deflated insertion configuration. Pressurization fluid is then fed to the collapsed balloon 16 via conduit or guide tubule 22 to inflate the balloon from the collapsed configuration to an expanded use configuration 24 shown in FIG. 2.

As shown in FIG. 2, balloon 16 has a pair of expandable or inflatable end members 26 and 28 and a plurality of expandable or inflatable spacer rods 30 connecting the end members to one another. Spacer rods 30 connect the end members 26 and 28 to one another so that the end members and the spacer rods are parts of the same unitary balloon structure 16 and so that the end members communicate with one another via the spacer member. In the inflated or expanded configuration of balloon 16, rods 30 push end members 26 and 28 away from one another, thus generating a retractor action tending to longitudinally spread tissues of the inner wall of colon CLN. In addition, end members 26 and 28 are expanded in a transverse direction so as to come into a frictional or clamping contact with the inner surface of the colon CLN.

Spacer rods 30 are disposed along one side of the retractor balloon or bladder 16. An opposing side (lower side in FIG. 2) is thus left open and unobstructed to facilitate an approach of the distal end of endoscope insertion member 14 to a polyp PLP or other site of interest along the inner wall of colon CLN. In general, spacer rods 30 are disposed so as not only to spread and hold end members 26 and 28 away from one another but also to facilitate the performance of an endoscopic diagnostic investigation or surgical operation on stretched and exposed organic tissues in the spaces between the rods. The surgeon is provided with sufficient room to work without the retractor obstructing the field.

End members 26 and 28 have a circular configuration adapted to uniformly engage the cylindrical inner surface or lumen of colon CLN. At least one end member 28 has a toroidal or ring shape defining an opening 32 traversed by endoscope insertion member 14, as shown in FIG. 2) after deployment of the retractor balloon 16. In deployment, balloon 16 smooths out folds (not shown) in the inner wall of colon CLN, thus enabling a user access to irregularities such as a polyp PLP. The other end member 26 of balloon 16 preferably has no traversable aperture like opening 32. Instead, where end member 26 is formed as a toroidal body 34 with an aperture 36, that aperture is covered by a membrane or screen 38 (collectively "membrane") for preventing the polyp PLP from rolling away from endoscope insertion member 14 should the polyp be severed from the colon in the course of a snare cauterization operation. Membrane 38 may additionally serve to entrain a severed polyp during a removal of the retractor balloon 16, thus acting as a capture pouch or retrieval device.

Upon the inflation of balloon 16 and prior to the passing of the distal end of endoscope insertion member 14 through opening 32, inflation conduit or tubule 22 may be severed proximately to the expanded balloon, at an end 40 of a nipple or nub element 42. To that end, nipple 42 may be provided at its point of connection to tubule 22 with a frangible section (not separately illustrated) for facilitating the detachment of the tubule. The breaking of the connection may be achieved by twisting tubule 22 or by cutting the frangible section with an endoscopic scissors (not shown) inserted through the endoscope biopsy channel.

Alternatively, tubule 22 may be connected to nipple 42 via any equivalent method, such as a threaded coupling, a force-lock fit, or a snap-on coupling (none separately illustrated). In the case of a threaded or screw coupling, detachment of tubule 22 from nipple 42 is implemented by turning the tubule from the proximal end thereof. Of course, tubule 22 would be made of a material with a sufficient rigidity to transmit the twisting torque from the proximal end outside the patient to the distal end at nipple 42. In the case of a force-lock fit, a separate rod or the distal end of the endoscope may be used to hold the nipple 42 while the tubule 22 is pulled in a proximal direction.

In order to prevent the escape of pressurization fluid from balloon 16 after the detachment of tubule 22, nipple 42 is provided with a one-way valve 44. It is to be noted that valve 44 may be alternatively disposed inside balloon or bladder 16 rather than in nipple 42.

As mentioned above, end members 26 and 28 expand radially or transversely to a longitudinal axis of the balloon 16 and transversely to the colon CLN. In order to enhance the gripping of the colon wall by end members 26 and 28. This transverse expansion of the instrument enables the application of pressure to the colon wall or other portion of a digestive tract to expand the organ and smooth out folds. To facilitate the gripping of the colon wall by end members 26 and 28, those members may be formed with outwardly protruding barbs, nubs, teeth or fingers (not shown).

At least one of the elongate spacer members 30 of retractor balloon or bladder 16 may be provided with a semi-rigid stiffener rod (not shown) which facilitates ejection of the balloon or bladder from the distal end of the insertion or deployment tube 12 by pusher rod 18.

After termination of the diagnostic or treatment procedures carried out via the endoscope, the balloon 16 is at least partially deflated simply by pucturing the balloon with a hot snare, a hot biopsy forceps, an endoscopic scissors or cutting device (not shown). The deflated balloon may be gripped by an endoscopic grasper or biopsy forceps (not shown) and dragged out of the patient with the endoscope insertion member. Where a severed polyp is to be removed with the retractor balloon 16 acting as a capture pouch, it may be desirable to retain a certain degree of pressurization of balloon 16 so that the trailing end member 26 retains some of its expanded form. In that case, limited depressurization of balloon 16 may be achieved by reattachment of tubule 22 to nipple 42 and use of an attached syringe (not shown) to extract a portion of the liquid or gas in balloon 16.

Where a severed polyp is extracted separately, for instance, using a retrieval pouch or snare, it is possible in at least some case to leave the deflated retractor balloon 16 inside the colon for evacuation with the patient's stool in due course subsequent to the endoscopic procedure.

Figure 4:
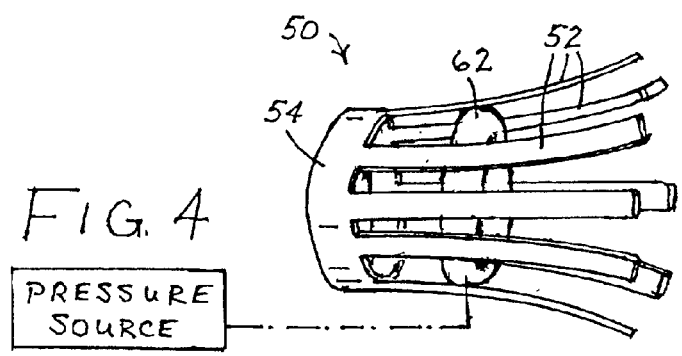
FIG. 4 is a schematic perspective view of the expandable member of FIG. 3, showing that member is an expanded use configuration.
Figure 3:
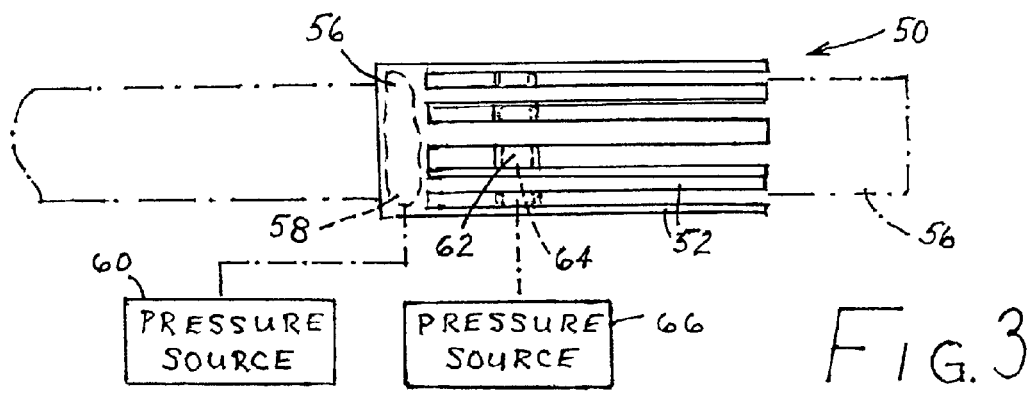
FIG. 3 is a schematic side elevational view of another endoscopic retractor instrument assembly in accordance with the present invention, showing an expandable member in a collapsed insertion configuration.

Another embodiment of a retractor instrument assembly 50 for use in flexible endoscopic investigations is depicted inn FIGS. 3 and 4. Generally, the endoscopic retractor instrument assembly 50 a plurality of prongs or finger parts 52 movably connected to one another via a ring-shaped base 54 made of substantially rigid material such as stainless steel. Prongs 52 normally assume, in the absence of external forces, a straight linear configuration, as shown in FIG. 3, so that the prongs are parallel to one another and disposed in a cylindrical configuration. In this configuration of prongs 52, the retractor assembly may be mounted to an outer surface of a flexible endoscope insertion member 56. Prongs 52 have sufficient flexibility so as the accommodate any bending that endoscope member 56 may undergo during an endoscopic medical procedure.

The endoscope retractor assembly 50 of FIGS. 3 and 4 further includes a toroidal balloon 58 attached to an inner surface of ring-shaped base 54 for enabling a releasable clamping of the retractor assembly to endoscope insertion member 56. To that end, balloon 58 communicates with a pressure source 60 such as a syringe.

Retractor assembly 50 additionally comprises an actuator in the form of a toroidal balloon 62 mounted on an exterior side of a rigid sleeve or collar 64 rigidly fixed to base 54. A pressure source 66 is operatively coupled with balloon 62 for inflating the same to push prongs 52 in a radially outward direction, whereupon the retractor assembly 50 assumes the flared expanded configuration of FIG. 4.

Upon arrival of the distal end of endoscope insertion member 56 at a desired site inside a patient, pressure source 66 is activated to pressurize balloon 62, thereby pressing prongs 52 outwardly to grip the lumen wall of a colon CLN (FIG. 2). At that point, pressure source 60 is operated to deflate balloon 58 from an expanded clamping configuration, thereby enabling a sliding of the endoscope insertion member 56 relative to the retractor assembly 50. The expanding of retractor assembly 50 spreads the walls of the colon and facilitates visual inspection of the colon via the optics of the endoscope.

Enhanced retraction action with the retractor assembly 50 of FIGS. 3 and 4 may be attained by utilizing two such assemblies, One or more rods (not shown) may be provided for spacing the two assemblies at a distance effective to longitudinally spread the tissues of the colon.

If considered necessary by the endoscopist, a flexible sleeve in the form of a cylindrical membrane or film (not shown) may be disposed over retractor assembly 50 and endoscope insertion member 56 during an insertion procedure, to protection the colon. Upon arrival of the distal end of the insertion member 56 at the desired site inside the patient, the sleeve is pulled in the proximal direction to uncover the retractor assembly or assemblies 50.

Figure 5:
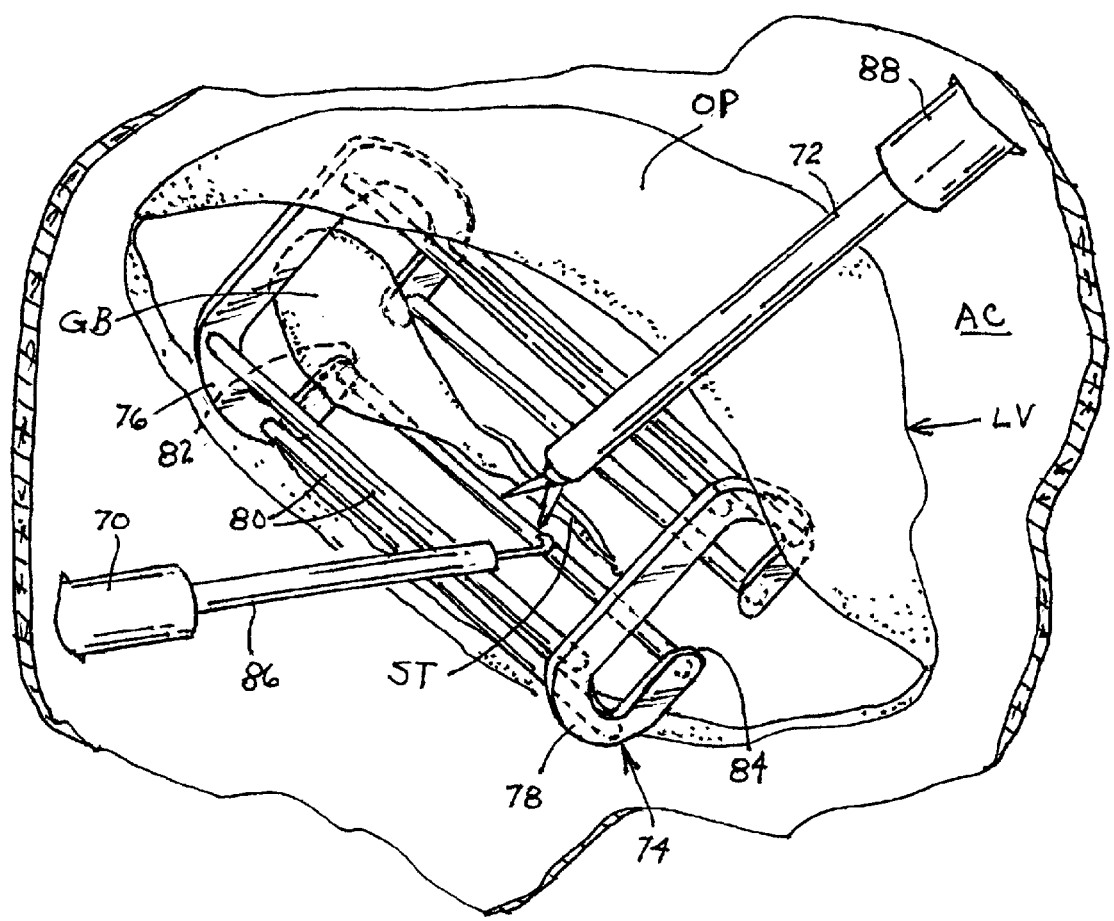
FIG. 5 is a schematic perspective view of a modified balloon or bladder retractor, showing the balloon or bladder retractor in an inflated use configuration inside an abdominal cavity, retracting a liver away from a gall bladder during performance of a laparoscopic cholecystectomy.

FIG. 5 depicts an endoscopic retractor 74 in an inflated use configuration in an abdominal cavity AC of a patient.

More particularly, retractor 74 is deployed around a gall bladder GB to prop open and separate the surrounding liver LV from the gall bladder. As discussed above with reference to retractor balloon 16 of FIGS. 1 and 2, retractor 74 is an inflatable balloon inserted in a collapsed configuration through an endoscopic device such as a laparoscopic cannula or trocar sleeve 70. As further discussed above with reference to FIGS. 1 and 2, retractor 74 may be disposed in the collapsed configuration inside a distal end portion of an insertion or deployment tube (not shown). The collapsed retractor 74 may be pushed out of the insertion or deployment tube by a pusher rod (not shown) upon a passing of the insertion or deployment tube through cannula 70.

Upon the introduction of the collapsed retractor 74 in abdominal cavity AC, the retractor is manipulated by laparoscopic forceps 72 into a suitable position adjacent to the liver LV in the area of the gall bladder GB. The expansion of retractor 74 from the collapsed configuration to the expanded configuration shown in FIG. 5 is accomplished by the procedures described above.

Retractor 74 has a pair of expandable or inflatable C-shaped end members 76 and 78 and a plurality of expandable or inflatable spacer rods 80 connecting the end members to one another. In the inflated or expanded configuration of balloon retractor 74, rods 80 push end members 76 and 78 away from one another, thus generating a retractor action tending to longitudinally spread tissues of liver LV. In addition, end members 76 and 78 are expanded in a transverse direction so as to push an overhanging portion OP of liver LV away from gall bladder GB. In most procedures, the retractor 74 is inserted in a collapsed or partially inflated condition around bladder GB. Completion of the inflation proceeds thereafter to lift overhanging portion OP up and away from the bladder GB.

End members 76 and 78 are provided with respective slots 82 and 84 because a stump ST of the gall bladder GB is connected to the liver LV. Most of a cholecystectomy procedure is directed to isolating the stump ST, which contains three critical structures, namely, the cystic duct, the cystic artery and the cystic vein (not separately illustrated). Those three structures must be separated and individually clamped and cut prior to a severing of the bladder's stump ST. Slots 82 and 84 enable a deployment of retractor 74 about the gall bladder GB.

End members 76 and 78, as well as end members 26 and 28, do not necessarily have a toroidal or circular configuration. Other geometric forms are possible, including rectangular, triangular, hemispherical, kidney-shaped, etc.

Retractor 74 may remain in abdominal cavity AC during an entire endoscopic procedure, after the retractor has been installed under overhanging liver portion OP, without support by or connection to any cannula 70 or 88. Those cannulas may then be used for the deployment of other laparoscopic instruments such as a cauterization probe or cutting element 86. There is no need to dedicate or relegate a cannula 70 or 88 to the retraction of overhanging liver portion OP. Of course, a connection of balloon retractor 74 to or through a cannula 70 may be retained to facilitate a repositioning of the retractor during the operation.

Retractor 74 may be used for other kinds of operations in rigid endoscopy, such as laparoscopic Nissan Fundoplication and laparoscopic colon resections.

Although the invention has been described in terms of particular embodiments and applications, one of ordinary skill in the art, in light of this teaching, can generate additional embodiments and modifications without departing from the spirit of or exceeding the scope of the claimed invention. For instance, retractor balloon 16 may be formed with a single spacer element such as a cylindrical section instead of a plurality of inflatable spacer rods 30. Another embodiment of a retractor instrument for use in flexible endoscopy such as colonoscopy is a chain of substantially rigid cylindrical parts connected to each other in an expandable cylindrical configuration by pivoting links. The pivoting links may be connected to a screw actuator. Like the embodiment of FIGS. 3 and 4, this embodiment would be mounted to the outer surface of the flexible endoscope insertion member. Typically, the retractor is separable from the insertion member inside the patient, to facilitate the further manipulation of the endoscope. However, as discussed above with reference to FIGS. 3 and 4, two such linkage-type retractor instrument may be mounted to the endoscope insertion member with one of the instruments longitudinally fixed to the endoscope and the other instrument detached and spaced at a variable distance.

Membrane 38 may be omitted in cases where retractor balloon 16 is used as a stiffener for a tortuous colon. In such cases, the endoscope insertion member 14 is manipulated, after the deployment of retractor balloon 16, to traverse opening 32 and aperture 36 during the passage of insertion member 14 to a located further upstream in the patient's colon CLN.

Accordingly, it is to be understood that the drawings and descriptions herein are proffered by way of example to facilitate comprehension of the invention and should not be construed to limit the scope thereof.

What is claimed is:

1. An endoscopic retractor instrument assembly comprising:
   an insertion or deployment tube insertable through a channel of an endoscopic instrument;
   a balloon or bladder having a pair of expandable or inflatable end portions and at least one expandable or inflatable spacer portion connecting said end portions to one another so that said end portions and said spacer portion are parts of the same unitary balloon structure and so that said end portions communicate with one another via said spacer portion, said balloon or bladder being disposed in a collapsed configuration inside said tube; and
   inflation means operatively coupled with said balloon or bladder for inflating said balloon or bladder from said collapsed configuration to an expanded use configuration in which said spacer portion pushes said end portions apart from one another.

2. The retractor instrument assembly defined in claim 1 wherein said inflation means includes an additional tube connected to said balloon or bladder.

3. The retractor instrument assembly defined in claim 2 wherein said inflation means further includes a one-way valve disposed between said additional tube and said balloon or bladder.

4. The retractor instrument assembly defined in claim 3 wherein said valve is disposed in a nipple or nub element connected to said balloon or bladder.

5. The retractor instrument assembly defined in claim 4 wherein said additional tube is removably connected to said nipple or nub element.

6. The retractor instrument assembly defined in claim 1 wherein said inflatable end portions are toroidal.

7. The retractor instrument assembly defined in claim 6 wherein said spacer portion is one of a plurality of elongate expandable or inflatable spacer members each having one end connected to and communicating with one of said end portions and an opposite end connected to and communicating with another one of said end portions.

8. The retractor instrument assembly defined in claim 6 wherein one of said inflatable end portions has a central aperture and is provided with a membrane extending across said aperture to close said aperture and prevent passage of objects through said aperture.

9. The retractor instrument assembly defined in claim 1 wherein said spacer portion is one of a plurality of elongate expandable or inflatable spacer portions each having one end connected to and communicating with one of said end portions and an opposite end connected to and communicating with another one of said end portions, said spacer portions being spaced from each other to provide unobstructed access to an interior wall of an organ.

10. An endoscopic retractor instrument assembly comprising:

an insertion or deployment tube insertable through a channel of an endoscopic instrument;

a balloon or bladder including a pair of expandable or inflatable end members and at least one expandable or inflatable spacer member connecting said end members to one another so that said end members and said spacer member communicate with one another, said balloon or bladder being disposed in a collapsed configuration inside said tube; and inflation means operatively coupled with said balloon or bladder for inflating said balloon or bladder from said collapsed configuration to an expanded use configuration, at least one of said end members being formed with an aperture or opening traversable by an endoscope insertion member of the endoscopic instrument after an inflation of said balloon or bladder from said collapsed configuration to said expanded use configuration.

11. The retractor instrument assembly defined in claim 10 wherein said inflation means includes an additional tube connected to said balloon or bladder.

12. The retractor instrument assembly defined in claim 11 wherein said additional tube is removably connected to said nipple or nub element.

13. The retractor instrument assembly defined in claim 10 wherein said spacer member is one of a plurality of elongate expandable or inflatable spacer members each having one end connected to and communicating with one of said end members and an opposite end connected to and communicating with another one of said end members.

14. The retractor instrument assembly defined in claim 13 wherein said spacer members are spaced from each other to provide unobstructed access to an interior wall of an organ.

15. The retractor instrument assembly defined in claim 10 wherein said inflatable end members are toroidal and said opening is circular.

16. The retractor instrument assembly defined in claim 10 wherein another one of said inflatable end members has a central aperture and is provided with a membrane extending across said aperture to close said aperture and prevent passage of objects through said aperture.

17. An endoscopic retractor instrument assembly comprising:

an insertion or deployment tube insertable through a channel of an endoscopic instrument;

a balloon or bladder including a pair of expandable or inflatable end members and a plurality of expandable or inflatable spacer member connecting said end members to one another so that said end members and said spacer members communicate with one another, said balloon or bladder being disposed in a collapsed configuration inside said tube; and inflation means operatively coupled with said balloon or bladder for inflating said balloon or bladder from said collapsed configuration to an expanded use configuration, said spacer members being spaced from one another and asymmetrically disposed to provide an enlarged window or opening on one side to facilitate unobstructed access to an interior wall of an organ.

* * * * *